United States Patent [19]
Cottrell et al.

[11] Patent Number: 5,321,192
[45] Date of Patent: Jun. 14, 1994

[54] DEHYDROGENATION PROCESS

[75] Inventors: Paul R. Cottrell, Arlington Heights; Lester F. Smith, Jr., Itasca; Stephen W. Gohres, Chicago, all of Ill.

[73] Assignee: UOP, Des Plaines, Ill.

[21] Appl. No.: 989,319

[22] Filed: Dec. 11, 1992

[51] Int. Cl.$^5$ .............................................. C07C 5/333
[52] U.S. Cl. .................................. 585/659; 585/660; 585/661
[58] Field of Search .................. 585/654, 659

[56] References Cited
U.S. PATENT DOCUMENTS

| | | | |
|---|---|---|---|
| 3,360,586 | 12/1967 | Bloch et al. | 260/683.3 |
| 3,829,524 | 8/1974 | Senn, III et al. | 585/659 |
| 3,907,921 | 9/1975 | Winter | 260/683.3 |
| 4,430,517 | 2/1984 | Imai et al. | 585/660 |
| 4,438,288 | 3/1984 | Imai et al. | 585/660 |
| 4,599,471 | 7/1986 | Ward | 585/659 |
| 4,778,941 | 10/1988 | Tagamolila | 585/324 |
| 4,899,003 | 2/1990 | Manyik et al. | 585/659 |

Primary Examiner—Anthony McFarlane
Attorney, Agent, or Firm—Thomas K. McBride; John G. Tolomei; John G. Cutts, Jr.

[57] ABSTRACT

The activity, selectivity and yield of a dehydrogenation process used to produce olefins from normal paraffin hydrocarbons having 2 to 5 carbon atoms per molecule is improved by the introduction of an essentially constant level of water into the inlet of two or more beds of dehydrogenation catalyst.

8 Claims, No Drawings

DEHYDROGENATION PROCESS

FIELD OF THE INVENTION

The invention relates to a process for the catalytic dehydrogenation of paraffin hydrocarbons having 2 to 5 carbon atoms per molecule. It is more specifically related to a dehydrogenation process in which water is injected into two or more of the inlets of each catalytic dehydrogenation zone in admixture with the dehydrogenatable hydrocarbon at essentially a constant rate of water addition. The invention particularly concerns the improved activity, selectivity and yield of a dehydrogenation process.

BACKGROUND OF THE INVENTION

Processes for the production of olefinic hydrocarbons are very useful in the production of a great many products. Because of the commercial importance of olefin compounds, those skilled in the art of producing olefins are constantly searching for better and more economical methods to produce olefins.

In U.S. Pat. No. 3,360,586 (Bloch et al), a process is disclosed for reacting a straight-chain paraffinic hydrocarbon of from about 7 to about 20 carbon atoms per molecule in contact with a Group VIII noble metal catalyst supported on a nonacidic refractory inorganic oxide carrier, hydrogen and water in an amount of at least about 400 ppm based upon the hydrocarbon.

In U.S. Pat. No. 3,907,921 (Winter), a process is described wherein the activity of a used dehydrogenation catalyst is improved by an increase in the water concentration maintained in the reactants toward the end of the catalyst's life. More specifically, the process comprises injecting 5 to 25 weight ppm of water into a hydrocarbon feed stream comprising normal paraffins having 5 to 18 carbon atoms per molecule, passing the feed in admixture with a gaseous recycle stream over a dehydrogenation catalyst comprising a platinum component and an alkali or alkaline earth component supported on a porous alumina carrier material, and increasing the rate of water injection to a value of 25 to 125 weight ppm after at least 40% of normal paraffins which may be processed before the catalyst requires replacement have passed through the reaction zone.

In U.S. Pat. No. 4,430,517 (Imai et al), a process is disclosed for the dehydrogenation of $C_2$–$C_{30}$ hydrocarbon compounds in the presence of water injection of water in an amount of 1–20,000 wppm.

Even with the broad teaching of the prior art that the presence of water is desirable in the dehydrogenation of hydrocarbons, those skilled in the art of catalysis have believed that a platinum containing catalyst is poisoned by high levels of oxygenates by various mechanisms. Therefore, since water is an expected intermediate for the formation of oxygenates such as carbon monoxide, the addition of water or water precursors is viewed as a platinum catalyst depressant. Additionally, heavy oxygenates are thought to lead to the formation of gums or coke precursors. The presence of water in a dehydrogenation zone strips or removes chloride from the platinum catalyst to form hydrogen chloride and the water is converted to form carbon monoxide via the water shift reaction at dehydrogenation conditions. For these reasons, the introduction of water into a catalytic dehydrogenation zone is considered undesirable.

We have discovered that by introducing a relatively small amount of water or water precursor at the inlet of two or more beds of dehydrogenation catalyst, the performance of the catalyst is significantly increased without any perceptible adversity.

BRIEF SUMMARY OF THE INVENTION

The invention provides a process for the catalytic dehydrogenation of paraffin hydrocarbons having 2 to 5 carbon atoms per molecule wherein a constant low level of water or water precursor is introduced into the inlet of two or more catalytic dehydrogenation zones to provide improved selectivity and yield of the desired dehydrogenated hydrocarbon.

One embodiment of the present invention is a process for the catalytic dehydrogenation of paraffin hydrocarbons having 2 to 5 carbon atoms per molecule wherein the dehydrogenation is conducted in at least two dehydrogenation zones containing dehydrogenation catalyst and wherein the dehydrogenatable hydrocarbons are reheated between the dehydrogenation zones which process comprises the following steps: (a) injecting from about 10 to about 300 mole ppm of water or an equivalent water precursor, based on the hydrocarbon feed rate, into a hydrocarbon feed stream comprising paraffin hydrocarbon having 2 to 5 carbon atoms per molecule; (b) passing the resulting hydrocarbon feed stream containing water in admixture with a gaseous recycle stream through a first dehydrogenation reaction zone maintained at dehydrogenation conditions sufficient to convert paraffin hydrocarbon having 2 to 5 carbon atoms per molecule and containing a dehydrogenation catalyst comprising a platinum component and an alkali metal or alkaline earth metal component supported on a porous alumina carrier material; (c) heating the effluent from the first dehydrogenation reaction zone and injecting from about 10 to about 300 mole ppm of water or an equivalent water precursor, based on the hydrocarbon feed rate; (d) passing the resulting heated stream from step (c) through a second dehydrogenation reaction zone maintained at dehydrogenation conditions sufficient to convert paraffin hydrocarbon having 2 to 5 carbon atoms per molecule and containing a dehydrogenation catalyst comprising a platinum component and an alkali metal or alkaline earth metal component supported on a porous alumina carrier material; and (e) maintaining an essentially constant rate of water injection into the first and the second dehydrogenation reaction zone.

Other embodiments of the subject invention encompass further details such as preferred feedstocks, dehydrogenation catalysts and dehydrogenation operating conditions, all of which are hereinafter disclosed in the following discussion of each of these facets of the invention.

DETAILED DESCRIPTION OF THE INVENTION

Processes for the production of olefinic hydrocarbons are very useful in the production of a great number of petrochemical products as well as motor fuel blending components. The short chain paraffins having from 2 to 5 carbon atoms per molecule are often subjected to dehydrogenation to form the corresponding olefin. The normal paraffin hydrocarbon having 2 to 5 carbon atoms per molecule is preferably selected from the group consisting of ethane, propane, butane and pentane. The olefins, in turn, are used, for example, in the alkylation of isoparaffins or in the etherification of alcohols to make motor fuel blending components. A great many other uses for such olefinic hydrocarbons are known.

The preferred process used for the dehydrogenation of low carbon number paraffin hydrocarbons is quite simple and straightforward. Fresh hydrocarbon feed is combined with recycle hydrogen and recycled unconverted hydrocarbons. This forms a reactant stream which is passed through a bed of suitable catalyst maintained at the proper dehydrogenation conditions such as temperature, pressure and space velocity, and the effluent from the catalytic reaction zone is passed to a separation zone wherein the effluent is cooled and partially condensed.

At least a portion of the uncondensed material is recycled as recycle gas stream comprising high hydrogen and light hydrocarbon gases. The net hydrogen which is produced in the process is vented for use in other applications such as desulfurization. The separation zone produces a liquid stream containing the dehydrogenated and undehydrogenated hydrocarbons. The liquid stream is then separated to recover the dehydrogenated hydrocarbons from the unconverted hydrocarbons which may then be recycled.

In accordance with the present invention, the dehydrogenation of paraffin hydrocarbons having 2 to 5 carbon atoms per molecule is conducted in at least two catalytic dehydrogenation zones with reheating of the reactant stream between each of the catalytic dehydrogenation zones. In addition, water or a water precursor is introduced at essentially a constant rate into two or more of the inlets of each catalytic dehydrogenation zone in an amount from about 10 to about 300 mole ppm water based on the hydrocarbon feed rate to the catalyst beds. When a water precursor is introduced along with a hydrocarbon feed and hydrogen to a dehydrogenation zone containing dehydrogenation catalyst, the water precursor is rapidly converted to water. A water precursor is preferably any convenient oxygen-containing compound which performs according to the teachings contained herein and may be any low molecular weight alcohol or ether such as, for example, methanol, ethanol, propanol ethyl ether, methyl tert-butyl ether and isopropyl ether.

The dehydrogenation process of the present invention is preferably practiced with a catalyst comprising a platinum component, a Group IVA component, an alkali or alkaline earth component, a halogen component and a porous carrier material. The platinum component is preferably present in the catalyst in an amount, calculated on an elemental basis, of about 0.01 to about 5 weight percent; the Group IVA component is preferably present in an amount from about 0.01 to about 5 weight percent; the alkali or alkaline earth component is preferably present in an amount from about 0.01 to about 15 weight percent and the halogen component is present preferably in an amount from about 0.2 to about 15 weight percent.

The platinum component may be incorporated in the catalytic composite in any suitable manner such as, for example, by coprecipitation or cogelation, ion exchange or impregnation or deposition from a vapor phase or by light procedures either before, while or after other catalytic components are incorporated. The preferred method of incorporating the platinum component is to impregnate the carrier material with a solution or suspension of a decomposable compound of platinum. For example, the platinum may be added to the support by commingling the latter with an aqueous solution of chloroplatinic acid. Another acid, for example, nitric acid or other optional components, may be added to the impregnating solution to further assist in dispersing or fixing the platinum component in the final catalyst composite.

Regarding the Group IVA component, it may be selected from the group of germanium, tin or lead or mixtures thereof. Tin, however, is the preferred Group IVA component. We believe that the Group IVA component exists within the catalyst in an oxidation state above that of the elemental metal. The Group IVA component may be present as a compound such as the oxide, for example, or combined with the carrier material or with the other catalytic components. Preferably the Group IVA component is well dispersed throughout the catalyst. The Group IVA component generally will comprise about 0.01 to about 5 weight percent calculated on an elemental basis of the final catalyst composite. Preferably, the catalyst comprises about 0.2 to about 2 weight percent tin. The Group IVA component may be incorporated in the catalytic composite in any suitable manner such as, for example, by coprecipitation or cogelation, ion exchange or impregnation or by like procedures either before, while or after other catalytic components are incorporated. A preferred method of incorporating the tin component is cogelling it during preparation of the porous carrier material. For example, tin may be incorporated in an alumina carrier material by mixing a soluble tin compound such as stannous or stannic chloride with an alumina hydrosol, adding a gelling agent such as hexamethylenetetramine and dropping the mixture into an oil bath to form spheres containing alumina and tin. A preferred method of incorporating the germanium component is to impregnate the carrier material with a solution or suspension of a decomposable compound of germanium such as germanium tetrachloride dissolved in an alcohol. Likewise, the lead component, may be impregnated from a solution of lead nitrate and water.

Regarding the alkali or alkaline earth component, it may be selected from the group of cesium, rubidium, potassium, sodium and lithium or from the group of barium, strontium, calcium and magnesium or mixtures of components from either or both of these groups. Lithium, sodium, potassium, cesium and magnesium, however, are the preferred alkali or alkaline earth components. We believe that the alkali or alkaline earth component exists in the final catalytic composite in an oxidation state above that of the elemental metal. The alkali or alkaline earth component may be present as a compound such as the oxide, for example, or combined with the carrier material or with the other catalytic components.

Preferably, the alkali or alkaline earth component is well dispersed throughout the catalytic composite. The alkali or alkaline earth component generally will comprise about 0.01 to about 15 weight percent, calculated on an elemental basis, of the final catalytic composite. Preferably the catalyst comprises about 1 to 5 weight percent potassium. The alkali or alkaline earth component may be incorporated in a catalytic composite in any suitable manner such as, for example, by coprecipitation or cogelation, by ion exchange or impregnation, or by like procedures either before, while or after other catalytic components are incorporated. A preferred method of incorporating the potassium component is to impregnate the carrier material with a solution of potassium nitrate.

Regarding the porous carrier material, it is preferably a porous, adsorptive support with high surface area of from about 25 to about 500 m$^2$/g. The porous carrier material should be relatively refractory to the conditions utilized in the hydrocarbon conversion process. It is intended to include within the scope of our invention the use of carrier materials which have traditionally been utilized in hydrocarbon conversion catalysts. The preferred carrier material for the catalyst of the present invention is alumina, especially gamma alumina.

The preferred alumina carrier material may be prepared in any suitable manner from synthetic or naturally occurring raw materials. The carrier material may be formed in any desired shape such as spheres, pills, cakes, extrudates, powders, granules and it may be utilized in any particle size. A preferred shape of alumina is the sphere. A preferred particle size is about 1/16" in diameter, though particles as small as 1/32", or smaller, may be utilized.

The catalyst used in the present invention also preferably contains a halogen component. The halogen component may be either fluorine, chlorine, bromine or iodine or mixtures thereof. Chlorine and bromine are the preferred halogen components. The halogen component is generally present in a combined state with the porous carrier material. Preferably the halogen component is well dispersed throughout the catalytic composite. The halogen component will comprise from about 0.1 weight percent to about 15 weight percent calculated on an elemental basis of the final catalytic composite.

The halogen component may be incorporated in the catalytic composite in any suitable manner, either during the preparation of the carrier material or before, while or after other catalytic components are incorporated. For example, the alumina sol utilized to form the preferred aluminum carrier material may contain halogen and thus contribute at least some portion of the halogen content in the final catalyst composite. Also, the halogen component or portion thereof may be added to the catalyst composite during the incorporation of the carrier material with other catalyst components, for example, by using chloroplatinic acid to impregnate the platinum component.

Dehydrogenation conditions include a temperature of from about 752° F. (400° C.) to about 1652° F. (900° C.), a pressure from about 0.01 to about 10 atm. and a liquid hourly space velocity (LHSV—calculated on the basis of the volume amount, as a liquid at standard conditions, of hydrocarbon charged to the dehydrogenation zone per hour divided by the volume of the catalyst bed utilized in the dehydrogenation zone) of from about 0.1 to about 100 hr$^{-1}$. The hydrocarbons to be dehydrogenated are dehydrogenatable hydrocarbons having from 2 to 5 carbon atoms.

In accordance with the present invention, a dehydrogenatable hydrocarbon is contacted with two or more beds of catalyst in a dehydrogenation zone maintained at dehydrogenation conditions. This contacting may be accomplished in a fixed catalyst bed system, a moving catalyst bed system, a fluidized bed system or in a batch-type operation. A moving bed system is preferred. In this moving bed system the hydrocarbon feed stream is preheated to the desired reaction temperature, admixed with water or a water precursor and then passed into the first bed of catalyst contained in the dehydrogenation zone. The resulting effluent from the first bed of dehydrogenation catalyst is reheated and additional water or water precursor is introduced and the resulting admixture is reacted in a second bed of dehydrogenation catalyst. The dehydrogenation zone may itself comprise two or more separate catalyst beds with heating means therebetween to ensure that the desired reaction temperature can be maintained at the entrance to each catalyst bed. The hydrocarbon may be contacted with the catalyst bed in either upward, downward or radial flow fashion. Radial flow of the hydrocarbon through the catalyst beds is preferred for commercial scale reactors. The hydrocarbon may be in the liquid phase, a mixed vapor-liquid phase or the vapor phase when it contacts the catalyst beds. Preferably, the hydrocarbon is in the vapor phase.

Conditions in the dehydrogenation zone include a temperature of from about 400° C. to about 90° C., a pressure from about 0.1 to about 10 atm. and a liquid hourly space velocity of from about 0.1 to about 100 hr$^{-1}$. Generally, for normal paraffins, the lower the molecular weight, the higher the temperature required for comparable conversion. The pressure in the dehydrogenation zone is maintained as low as practicable, consistent with equipment limitations, to maximize the chemical equilibrium advantages.

The effluent stream from the dehydrogenation zone generally will contain unconverted dehydrogenatable hydrocarbons, hydrogen and the product of the dehydrogenation reactions. This effluent stream is typically cooled and passed to a hydrogen separation zone to separate a hydrogen-rich vapor phase from a hydrocarbon-rich liquid phase. Unconverted dehydrogenation hydrocarbons are recovered and may be recycled to the dehydrogenation zone. Products of the dehydrogenation reaction are recovered as final products or as intermediate products in the preparation of other compounds.

The dehydrogenatable hydrocarbons may be admixed with a diluent material before, while or after being passed to the dehydrogenation zone. Hydrogen is the preferred diluent. Ordinarily, when hydrogen is utilized as the diluent, it is utilized in amounts sufficient to ensure a hydrogen to hydrocarbon mole ratio of about 0.1:1 to about 40:1, with best results being obtained when the mole ratio range is about 1:1 to about 10:1. The diluent hydrogen stream passed to the dehydrogenation zone will typically be recycled hydrogen separated form the effluent from the dehydrogenation zone in the hydrogen separation zone.

In addition and in accordance with the process of the present invention, the feed to two or more of the catalyst zones is preferably adjusted to contain from about 10 mole ppm to about 300 mole ppm water or equivalent water precursor before the effluent from one catalyst zone is introduced into the next dehydrogenation catalyst zone.

The process of the present invention is further demonstrated by the following illustrative embodiment. This illustrative embodiment is, however, not presented to unduly limit the process of this invention, but to further illustrate the advantages of the hereinabove described embodiments. The following data were not obtained by the actual performance of the present invention, but are considered prospective and reasonably illustrative of the expected performance of the invention.

ILLUSTRATIVE EMBODIMENT

A dehydrogenation process unit having four sequential catalyst beds each containing about 25% of the total catalyst is loaded with a dehydrogenation catalyst containing a platinum component, a tin component, a potassium component and an alumina support. Since dehydrogenation is an endothermic reaction, there are interstage heaters which permit the reactants to be reheated before being introduced into the next bed of dehydrogenation catalyst.

A propane feedstock is charged to the dehydrogenation process unit described above and adjusted to produce 100 mass units per hour of propylene without water injection. Without any other changes to the dehydrogenation process, a water precursor compound is introduced into the inlet of the first bed of catalyst in an amount sufficient to produce a water concentration of 75 mole ppm based on the combined liquid feed and the production of propylene increases to 108 mass units per hour. The dehydrogenation process is then operated with a water concentration of 75 mole ppm based on the combined liquid feed at the inlet to the first bed of catalyst and a water precursor compound is introduced into the inlet of the third bed of catalyst in an amount sufficient to produce a water concentration of 75 mole ppm based on the combined liquid feed and the production of propylene increases to 113 mass units per hour. These results are summarized and presented in Table 1.

TABLE 1

| | PROPYLENE PRODUCTION | | |
| --- | --- | --- | --- |
| | No Water | Single Stage Water Injection | Two-Stage Water Injection |
| Propylene Production, mass units per hour | 100 | 108 | 113 |

The foregoing description and illustrative embodiment clearly illustrate the advantages encompassed by the process of the present invention and the benefits to be afforded with the use thereof.

What is claimed:

1. A process for the catalytic dehydrogenation of paraffin hydrocarbons having 2 to 5 carbon atoms per molecule wherein said dehydrogenation is conducted in at least two dehydrogenation zones containing dehydrogenation catalyst and wherein the dehydrogenatable hydrocarbons are reheated between said dehydrogenation zones which process comprises the following steps:

(a) injecting from about 10 to about 300 mole ppm of water or an equivalent water precursor in a constant and continuous manner, based on the hydrocarbon feed rate, into a hydrocarbon feed stream comprising paraffin hydrocarbon having 2 to 5 carbon atoms per molecule;

(b) passing the resulting hydrocarbon feed stream containing water in admixture with a gaseous recycle stream through a first dehydrogenation reaction zone maintained at dehydrogenation conditions sufficient to convert paraffin hydrocarbon having 2 to 5 carbon atoms per molecule and containing a dehydrogenation catalyst comprising a platinum component and an alkali metal or alkaline earth metal component supported on a porous alumina carrier material;

(c) heating the effluent from said first dehydrogenation reaction zone and injecting from about 10 to about 300 mole ppm of water or an equivalent water precursor, based on the hydrocarbon feed rate;

(d) passing the resulting heated stream from step (c) through a second dehydrogenation reaction zone maintained at dehydrogenation conditions sufficient to convert paraffin hydrocarbon having 2 to 5 carbon atoms per molecule and containing a dehydrogenation catalyst comprising a platinum component and an alkali metal or alkaline earth metal component supported on a porous alumina carrier material; and (e) maintaining an essentially constant rate of water injection into said first and said second dehydrogenation reaction zone.

2. The process of claim 1 wherein said normal paraffin hydrocarbon having 2 to 5 carbon atoms per molecule is selected from the group consisting of ethane, propane, butane and pentane.

3. The process of claim 1 wherein said dehydrogenation conditions include a pressure from about 0.01 to about 10 atmospheres, a liquid hourly space velocity from about 0.1 to about 100 hr$^{-1}$ and a temperature from about 752° F. (400° C.) to about 1652° F. (900° C.).

4. The process of claim 1 wherein said dehydrogenation catalyst comprises an alkali metal component selected from the group consisting of lithium, sodium and potassium.

5. The process of claim 1 wherein said dehydrogenation catalyst comprises an alkaline earth metal selected from the group consisting of magnesium, calcium, strontium and barium.

6. The process of claim 1 wherein said dehydrogenation catalyst comprises a component selected from the group consisting of tin and germanium.

7. The process of claim 1 wherein said water precursor is selected from the group consisting of alcohols and ethers.

8. The process of claim 1 wherein said water precursor is selected from the group consisting of methanol, ethanol, propanol, ethyl ether, methyl tert-butyl ether and isopropyl ether.

* * * * *